United States Patent [19]

Barberet et al.

[11] Patent Number: Plant 5,515

[45] Date of Patent: Jul. 16, 1985

[54] CARNATION NAMED LONDAPO

[75] Inventors: Nicole Barberet; Yves Ducloux, both of Antibes, France

[73] Assignee: Laboratoire de Physiologie Vegetale de la Londe, La Londe, France

[21] Appl. No.: 516,515

[22] Filed: Jul. 25, 1983

[51] Int. Cl.[3] ..... A01H 5/00

[52] U.S. Cl. ..... Plt./71

[58] Field of Search ..... Plt./71

*Primary Examiner*—Robert E. Bagwill

*Attorney, Agent, or Firm*—Chas. W. Rummler

[57] ABSTRACT

A distinctive carnation cultivar particularly distinguished by its medium sized flowers of phlox pink coloration, which are borne on long, erect and rigid stems and which bloom profusely during the recurrent blooming seasons of Spring and Fall. This plant has a vigorous, upright growth habit with moderately abundant foliage and a height averaging about 120 cm. at eight months.

1 Drawing Figure

BACKGROUND OF THE NEW PLANT

This new carnation cultivar is the result of breeding efforts carried on by us at La Londe, Les Maures, France, since 1978, and this new plant originated as a seedling produced by our crossing of selected and individually identified plants chosen from among our collection of exceptional carnation plants maintained at La Londe for breeding purposes. This particular seedling was selected by us for propagation and test because of its very lovely pink coloration and its apparently favorable growth habit. This discovery plant was reproduced by us at La Londe by means of cuttings of the parent and the plants developed from these cuttings appearing to be very favorable with respect to retention of the novel characteristics of the parent plant, we continued such propagation through several successive generations and determined that the novel and distinctive characteristics of the discovery plant were fully retained from generation to generation and appeared to be firmly fixed.

DESCRIPTION OF THE DRAWING

Our new carnation variety is illustrated by the accompanying photographic drawing which shows, in full color, a typical arrangement of buds and flowers in several stages of opening, the colors shown being as nearly true to those specified herein as is reasonably possible to obtain by conventional photographic procedures.

DESCRIPTION OF THE NEW PLANT

The following is a detailed description of our new carnation discovery based upon observations of greenhouse grown plants made at La Londe, France, in the Spring of 1983, the color designations being specified according to The R.H.S. Colour Chart published by The Royal Horticultural Society at London, England.

THE PLANT

Origin: Seedling.

Parentage:

*Seed parent.*—Stock Plant No. 73 L 1 (unpatented).

*Pollen parent.*—Stock Plant No. 85 17 L (unpatented). These unnamed varieties are individually identified in our permanent records and are maintained for breeding purposes in our collection of carnation plants at La Londe, France.

Classification:

*Botanic.*—Dianthus caryphyllus.

*Commercial.*—Standard Carnation.

Form: Tall, erect bush with at least four stems being emitted near the ground.

Height: Averages about 120 cm. at eight months.

Main stem:

*Length.*—Less than 15 cm. due to pinching.

Branching character: Branches are few.

Growth habit: Vigorous, upright and rigid.

Foliage:

*Quantity.*—Moderately abundant.

*Number of leaves.*—More than 120.

*Leaf size.*—Averaging about 11.5 cm. long and about 1.2 cm. wide at the seventh node.

*Leaf shape.*—Spindel shaped with rounded margins.

*Texture.*—Leathery.

*Color.*—Upper side — 189A. Under side — 189A.

*Ribs and Veins.*—Hardly noticeable.

*Rachis.*—Hardly noticeable.

THE BUD

Form: Globular.

Size: Medium.

*Diameter.*—Averages about 2.1 cm.

*Length.*—Averages about 3.2 cm.

Opening rate: Normal for carnations.

Color of petals:

*When sepals first divide.*—Slightly darker than at full bloom.

*When petals begin to unfurl.*—The color is about the same.

Sepals:

*Number.*—Five or six.

*Shape.*—The sepals are joined at the lower part and the upper part is of acute character with a sharply pointed apex. The sepals are hooded over the bud and stand up when the flowers open.

*Color.*—Inside — Greenish white. Outside — 138B and 145A.

*Striae.*—Longitudinal.

Calyx:

*Size.*—Large.

*Shape.*—Almost cylindrical.
*Splitting.*—The calyx very rarely splits.
*Aspect.*—Smooth.

Flower stem:
*Length.*—About 70 cm.
*Character.*—Erect and rigid.
*Color.*—189B and 137C.

THE FLOWER

Blooming habit: Recurrent and profuse during the mid-season of Spring and Fall.

Size of bloom: Medium.
*Diameter.*—Averages about 8.3 cm.
*Depth.*—Averages about 5.7 cm.

Borne: Singly.

Shape:
*When bloom first opens.*—High centered.
*When bloom matures.*—Ball-shaped.

Petalage:
*Number of petals.*—Averages about 56.
*Arrangement.*—Imbricated.
*Form.*—Widely opened fan with very pronounced serrations at its outer margin.
*Texture.*—Soft.
*Appearance.*—Satiny.
*Color.*—Outer Petal: Body — 62B and 64D. Base — Greenish. Reverse side — 63D and 65B. Inside Petal: Body — 62B and 64D. Base — Greenish. Reverse side — 63D and 65B.

General appearance of bloom: The darker colors are not uniformly distributed on the petal and may appear as spots or streaks and at the petal tips, the principal petal body color being Phlox Pink 62B.

Petaloids:
*Number.*—From 3 to 9.

*Size.*—Smaller than the petals.
*Color.*—The same as the petals.

Flower stem:
*Length.*—About 70 cm. (cut at the tenth node).
*Character.*—Upright and of good strength.
*Color.*—189B and 137C.

Fragrance: A fragrance is present.

Persistence: The petals hang on and dry.

Lasting quality:
*As a cut flower.*—At least ten days in vase keeping.

Disease resistance: This plant appears to be resistant to *Fusarium oxysporum* as observed INRA, Antibes, Alpes-Maritimes, France.

REPRODUCTIVE ORGANS

Stamens:
*Number.*—7 To 13.
*Arrangement.*—Encircling the pistils.
*Anthers.*—Size: Less than 4 mm. Color: Whitish.
*Filaments.*—Color — Whitish.

Pistils:
*Number.*—3; Rarely 4.
*Styles.*—Color — White.
*Stigmas.*—Color — White.

Character of ovaries: Ovary shows a few ribs.

We claim:

1. A new and distinct carnation cultivar, substantially as herein shown and described, characterized by the very delicate phlox pink and magenta rose coloration of its medium sized blooms which are borne on long, strong, stiff stems; and by its advantageous growth habit and abundant production of flowers during its blooming seasons.

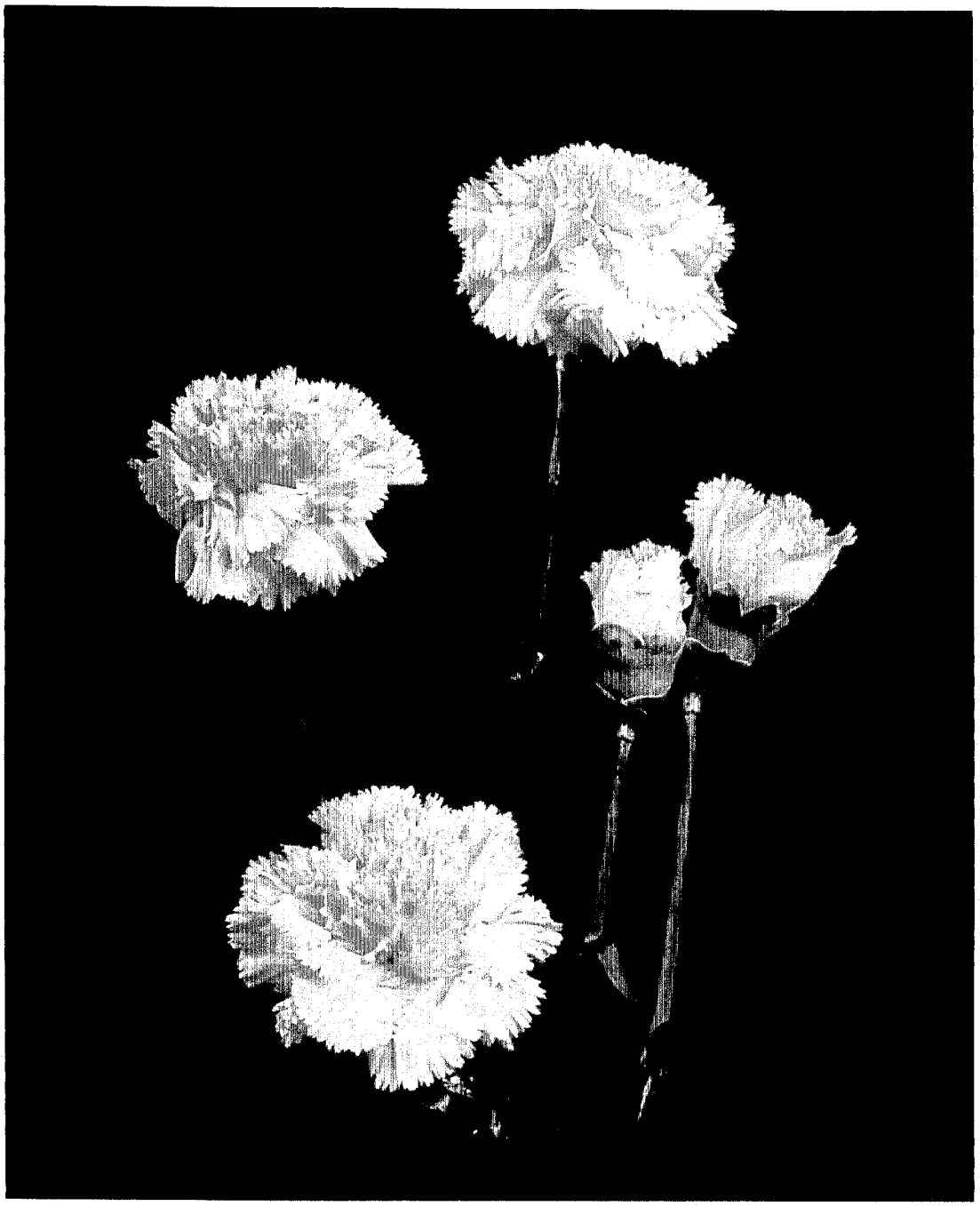

* * * * *